United States Patent [19]
Horváth nee Lengyel et al.

[11] 3,993,781
[45] Nov. 23, 1976

[54] 1,6-DIBROMO-1,6-DIDEOXY-DULCITOL AND PHARMACEUTICAL COMPOSITIONS CONTAINING SAME

[75] Inventors: Piroska Horváth nee Lengyel; László Institoris; Endre Csányi; László Vargha, all of Budapest, Hungary

[73] Assignee: Chinoin Gyogyszer-es Vegyeszeti Termekek Gyara RT, Budapest, Hungary

[22] Filed: Jan. 10, 1966

[21] Appl. No.: 519,440

[30] Foreign Application Priority Data
Jan. 13, 1965 Hungary.............................. GO 940

[52] U.S. Cl. ................................................ 424/343
[51] Int. Cl.$^2$ ........................................ A61K 31/045
[58] Field of Search .................... 167/78 C; 424/343

[56] References Cited
FOREIGN PATENTS OR APPLICATIONS
959,407   6/1964   United Kingdom ................ 424/343

OTHER PUBLICATIONS
Chemical Abstracts 45:6159f(1951).
Suguira, Cancer Research, vol. 25, No. 3, Part 2, Apr. 1965, pp. 494–496 and 501–512.

*Primary Examiner*—Jerome D. Goldberg
*Attorney, Agent, or Firm*—Blum, Moscovitz, Friedman & Kaplan

[57] ABSTRACT

This invention is directed to the preparation of a cytostatic sugar derivative, 1,6-dibromo-1,6-dideoxy-dulcitol and of pharmaceutical compositions containing same.

1 Claim, No Drawings

1,6-DIBROMO-1,6-DIDEOXY-DULCITOL AND PHARMACEUTICAL COMPOSITIONS CONTAINING SAME

This invention is directed to the preparation of a cytostatic sugar derivative. More particularly it is concerned with the preparation of 1,6-dibromo-1,6-dideoxy-dulcitol and of pharmaceutical compositions containing same.

It is known (British Pat. No. 959,407) that 1,6-dibromo-1,6-dideoxy-D-mannitol shows valuable cytostatic effect and according to clinical tests it may be used successfully for treatment of cases of myeloide leukaemia.

Our investigations have been extended to the alfa, omega-dibromo derivatives of other open chained compounds (alkanes and polyalkohols). We have come to the surprising conclusion that 1,6-dibromo-1,6-dideoxy-dulcitol (abbreviated further on as DBD) also possesses tumor-inhibiting properties and exibits a strong effect on the blood-picture. The effective doses of DBD are significantly smaller than those of 1,6-dibromo-1,6-dideoxy-D-mannitol.

The above is particularly surprising when taking into consideration that by investigating 1,6-dimethane-sulphonyl-D-mannitol (having similar therapeutical application to 1,6-dibromo-1,6-dideoxy-D-mannitol) Varga et al (Acta Chim. Hung. 25,361 /1960/ and Timmis et al (Biochem. Pharmacol. 3., 247, /1960/ found that the cytostatic effect was restricted to the stereostructure of D-mannitol and the dimethane-sulphonyl derivatives of other stereoisomeric hexitols — among them also the 1,6-dimethane-sulphonyl-dulcitol-proved to be ineffective.

The present invention provides a process for the preparation of 1,6-dibromo-1,6-dideoxy-dulcitol, being also suitable for the preparation of said compound on an industrial scale. Such a process has not been set forth in the prior art. Bouchardat Annales de Chimie 27,182 (1872) described the mere formation of DBD. According to his teaching 1 part of dulcitol was heated with 10 parts of aqueous hydrogen bromide (60 %, density: 1,7) in a closed system at 100° C. The reaction product obtained consisted of a great amount of amorphous anhydro and polybromo derivatives and contained also plate-formed crystals, the elementary analysis data of which approximated that of DBD. The article of Buchardat does not comprise any reference to the yields achieved. The author did not succeed in purifying the product and did not obtain a compound having a determined melting point. It is only disclosed that when heating the crystals above 100° C, hydrogen bromide is split off. Thus said product is not DBD, but an unidentified mixture.

According to the report described by P. Bladon et al (J. Chem. Soc. 1950, 3000) dulcitol is heated under reflux with fuming hydrobromic acid for 5 hours, whereupon the reaction mixture is evaporated and the residual thick syrup gives on triturature with ice-water a crystalline product. Yield 2.3 %. M.p.: 171°–174° C. The authors presumed that DBD was obtained in spite of the insufficient analysis data and the low melting point. We have found, that the high temperature used and the decreasing hydrogen bromide concentration due to the open system reaction cause destruction of the molecule.

It has been found according to the present invention that 1,6-dibromo-1,6-dideoxy-dulcitol may be advantageously prepared by reacting dulcitol with an aqueous hydrogen bromide solution containing more than 47 % of hydrogen bromide in a closed system under pressure at a temperature in the range of 60°–80° C for 9–0.5 hours.

The process according to the present invention may be carried out by using an aqueous hydrogen bromide solution containing preferably 69–70 % of hydrogen bromide. The reaction time is in inverse proportion to reaction temperature, e.g. when the reaction is accomplished at 60° C the yields increase when the reaction time amounts to 8–9 hours, while when the reaction is carried out at a higher temperature (80° C) a shorter reaction time of 0.5-1 hour is sufficient. The use of high temperature and long reaction time promotes namely the formation of overbrominated and anhydro products and results in the destruction of the molecule. The reaction according to the present invention may be illustrated by the following reaction equation:

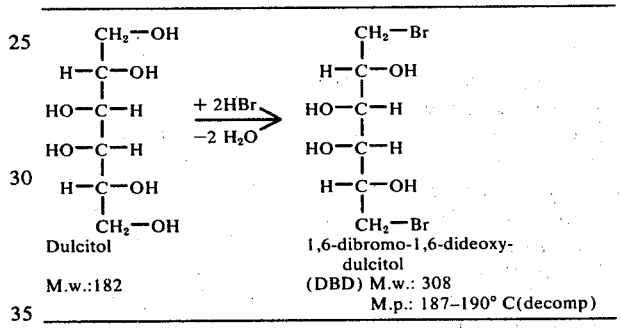

The yields amount to 60–70 % (calculated on the crude product), while the rate of recrystallization amount to 75–80 %. The crude product may be recrystallized from alcohols to yield a pure product having a well-defined melting point. The melting point of DBD has never been disclosed before.

According to a preferred form of realisation of the present invention the reaction is carried out with an aqueous hydrogen bromide solution containing 69–70 % of hydrogen bromide by using an excess of hydrogen bromide (10–15 moles of hydrogen bromide per one mole of dulcitol are applied). The reaction is accomplished in a closed system under pressure. The pressure applied is provided by the vapours of the reaction mixture and amounts to about 7–8 atm.

DBD is a poorly soluble crystalline compound, it is but slightly soluble in cold water or concentrated hydrogen bromide and practically insoluble in hydrocarbons or chlorinated solvents. DBD may be recrystallized from alcohols, such as hot methanol or ethanol. If DBD is heated with water, decomposition takes place.

A further feature of the present invention provides pharmaceutical compositions containing DBD as active ingredient. DBD exhibits a strong tumor-inhibiting effect in animal tests. The tumor-inhibiting effect of DBD is similar to that of DBM. However the effective doses of DBD are smaller and the inhibition achieved is higher than those of DBM. DBD also influences the myeloid elements of blood. The importance of DBD as an antitumor agent resides in the fact, that sooner or later a certain resistance is developed against the tumor inhibiting agents used, therefore the application of new drugs is required.

The pharmaceutical compositions according to the present invention contain DBD as active ingredient in admixture with solid or liquid, organic or inorganic therapeutically acceptable carriers, and/or excipients generally used for such preparations. Thus the following carriers may be applied: Lactose, ethyl cellulose, starch, talcum, magnesium stearate, propylene glycol, water, etc.

The pharmaceutical compositions according to the present invention are suitable for oral, rectal or parenteral administration. They may be finished in the form of tablets, coated pills, suppositories, injections, etc. The compositions may contain further auxiliary agents, such as filling, coating, sliding, emulsifying materials, etc. and also further therapeutically active compounds. It is preferred to administrate DBD in the form of tablets having an active ingredient content of 0.01–0.10 e.g. 0.05 g. The dosage depends on the haematological state of the patient.

Further details of the process are to be found in the Examples.

EXAMPLES 1. 140 g of dulcitol are suspended in 280 ml of a 48% aqueous hydrogen bromide solution, whereupon the solution thus obtained is saturated at a temperature below 0° C with gaseous hydrogen bromide until a hydrogen bromide content preferably above 69–70 % is achieved. 400–430 g of hydrogenbromide are adsorbed in the solution. The reaction mixture is heated for 5 hours at 70° C in an autoclave - the pressure amounts to 7–8 atm — whereupon it is poured on 1 kg of ice-water. The white, powdery precipitate is allowed to stand for some hours, whereupon it is filtered, washed until free of acid with cold water, than washed with cold methanol and dried at 50° C. Thus 166 g of crude dibromodulcitol are obtained.

Mp.: 183°–185° C. Yield: 70 %.

The crude product may be recrystallized from methanol or other alcohols, preferably admixed with chlorinated hydrocarbons. Aqueous alcohols or aqueous acetons may be used as recrystallisation solvent as well.

Thus pure 1,6-dibromo-1,6-dideoxy-dulcitol is obtained, m.p. 187°–188° C.

Analysis: Br % = 51,5, 52,0. (Calc.: 51,9).

The therapeutical effect of 1,6-dibromo-1,6-didesoxydulcitol is substantiated by the following Table:

(a) Tumour-inhibiting effect

| Doses mg/kg i.p. | Tumour | Inhibition % | Remarks |
|---|---|---|---|
| 1 × 500 | Yoshida asc. sarc. | 100 | Recovered 5/5 |
| 6 × 50 | Guerin s.c. sarc. | 61 | |
| 6 × 25 | S-180 s.c. sarc. | 27 | No decrease in body-weight |
| 6 × 25 | Yoshida s.c. sarc. | 96.4 | |
| 6 × 4 | Yoshida s.c. sarc. | 45.5 | |
| 6 × 0.5 | Yoshida s.c. sarc. | 0 | | b) Effect of 1,6-dibromo-1,6-dideoxy-D-dulcitol on the peripherial leucocyte-number of normal rats.
Doses: 1×300 mg/kg on the 0. day

| Days | 0 | 2 | 3 | 4 | 5 | 8 |
|---|---|---|---|---|---|---|
| Number of limphocytes | 14020 | 13600 | 11900 | 7510 | 11330 | 11700 |
| Alteration in the percentage of the original value | | −3 | −15 | −46.5 | −19 | −17 |
| Number of granulocytes | 2560 | 2040 | 1190 | 960 | 1840 | 4480 |
| Alteration in the percentage of the original value | | −20 | −53 | −62.5 | −28 | +75 |

The bioloical investigations were carried out on rats and mice. To determine the toxicity of the compounds we used male Swiss mice. The substances were suspended with Tween 80, and administered i.p. Each dose was injected to at least 5 mice, and each compound administered in at least five doses. $LD_{50}$ was determined with the probit method. Litchfield, J. T., Wilcoxon, F. W., J. Pharm. Exp. Ther. 96, 99 (1948).

The tumor inhibitory effect was tested on transplantable rat and mouse tumors. Female mice and C. B. Wister rats were used, 21–25 or 160–200 g in weight, respectively. In the case of solid tumors the tumor fragments were inoculated by the conventional trocar technic; the ascitic tumors were transplanted by injecting 0.2 ml of ascitic fluid into the peritoneal cavity. Injections of the test substance were begun 24 h after transplantation. After the test period the animals with solid tumors were killed and the tumor weight was measured. The inhibitory effect was expressed as the percentage inhibition of the tumor growth related to untreated groups. In the case of ascitic tumors the criteria of activity was the survival of the treated animals as compared to the controls. The following tumors were used. Yoshida subcutaneous sarcoma, Yoshida ascitic sarcoma, Guerin subcutaneous carcinoma (rat tumors); S-180 subcutaneous sarcoma, S-37 subcutaneous sarcoma, Ehrlich ascitic carcinoma (mice tumors).

The effect on the hemopoietic system was investigated on rats. The peripherical lymphocyte and granulocyte counts were carried out with usual laboratory methods.

| 2.)Tablet formulation | per 50 tablets |
|---|---|
| 1,6 dibromo-1,6-dideoxy-dulcitol | 2,5 g |
| Lactose | 2,425 g |
| Ethyl cellulose | 0,150 g |
| Amylum solani | 0,75 g |
| Talc | 0,125 g |
| Magnesium stearate | 0,05 g |
| One tablet weighs | 0,12 g |
| DBD content = | 0,05 g |

The active ingredient is admixed with the lactose in a suitable mixer and granulated with an alcoholic solution of the ethyl cellulose. The granulate is dried at 40° C and admixed with the other ingredients, whereupon the mixture is pressed into tablets.

What we claim is:

1. Method of achieving cytostatic action, which comprises administering to a host an effective cytostatic amount of 1,6-dibromo-1,6-dideoxy-D-dulcitol having a m.p. of 187°–190° C.

* * * * *